United States Patent [19]
Adkins et al.

[11] Patent Number: 5,739,397
[45] Date of Patent: Apr. 14, 1998

[54] PROCESS FOR THE PRODUCTION OF SECONDARY AMINES AND THE AMINES PRODUCED BY THE PROCESS

[75] Inventors: Rick L. Adkins, New Martinsville; William E. Slack, Moundsville, both of W. Va.

[73] Assignee: Bayer Corporation, Pittsburgh, Pa.

[21] Appl. No.: 655,638

[22] Filed: May 30, 1996

[51] Int. Cl.⁶ .................................... C07C 209/22
[52] U.S. Cl. .................... 564/408; 564/445; 564/454; 564/469; 544/402
[58] Field of Search .................... 564/481, 408, 564/445, 454, 469; 544/402

[56] References Cited

U.S. PATENT DOCUMENTS

| | | | |
|---|---|---|---|
| 3,654,370 | 4/1972 | Yeakey | 260/584 B |
| 3,666,726 | 5/1972 | Grogler et al. | 260/77.5 CH |
| 3,691,112 | 9/1972 | Grogler et al. | 260/2.5 AM |
| 3,780,107 | 12/1973 | Polanskyj et al. | 260/583 |
| 3,933,717 | 1/1976 | Shinohara et al. | 260/29.6 R |
| 4,643,953 | 2/1987 | Gurgiolo et al. | 428/520 |
| 4,902,768 | 2/1990 | Gerkin et al. | 528/68 |
| 5,015,774 | 5/1991 | Suekane et al. | 564/475 |
| 5,041,668 | 8/1991 | Nalepa et al. | 564/330 |
| 5,043,472 | 8/1991 | Mafoti | 560/358 |
| 5,171,819 | 12/1992 | Su et al. | 528/73 |

*Primary Examiner*—Brian M. Burn
*Attorney, Agent, or Firm*—Joseph C. Gil; Lyndanne M. Whalen

[57] ABSTRACT

Secondary amines having a hydrocarbon backbone, a functionality of at least 1 and a molecular weight of at least 74 are produced by reacting a hydrocarbon containing a leaving group with a primary amine, primary diamine, primary polyamine or ammonia at a temperature of from about 70° to 250° C.

5 Claims, No Drawings

PROCESS FOR THE PRODUCTION OF SECONDARY AMINES AND THE AMINES PRODUCED BY THE PROCESS

BACKGROUND OF THE INVENTION

The present invention relates to a process for producing secondary amines having a hydrocarbon backbone which amines are particularly suitable for use in the production of polyurethanes and polyureas and to the amines produced by this process.

Amines and various processes for preparing amines are known in the art. Amines are of particular interest in the production of materials such as polyurethanes and polyureas. Amine-terminated polyethers, processes for their production and use in polyurethane applications have been the subject of a number of prior art disclosures.

U.S. Pat. No. 3,654,370, for example, discloses amine-terminated polyethers which are prepared by reacting polyols with ammonia under catalyzed high temperature reaction conditions.

U.S. Pat. Nos. 3,666,726, 3,691,112, and 5,043,472 disclose amine-terminated polyethers which are prepared by reacting a polyfunctional acetoacetic acid ester with a polyfunctional amine.

U.S. Pat. No. 5,171,819 discloses a process for the production of a polyurea elastomer in which an amine-terminated polyoxyalkylene polyol and an alkyl substituted piperazine are reacted with an isocyanate.

U.S. Pat. No. 4,902,768 discloses N-(polyoxyalkyl)-N (alkyl)amine by catalytic amination of an appropriate polyol by reacting the polyol with a primary or secondary amine in the presence of a catalyst such as nickel.

U.S. Pat. No. 5,015,774 discloses a process for preparing polyoxyalkylene polyamines having secondary amino groups at the end of the polyamine by reacting polyoxyalkylene polyol with a primary amine in the presence of a catalyst containing nickel and zinc, cobalt and zinc or cobalt, zinc and nickel.

The use of secondary amines containing no ether, polyester or other non-hydrocarbon linkage for the production of polyurethanes and polyureas is also of interest in the production of polyurethanes and polyureas. However, because hydrocarbon-based secondary amines having no non-carbon/hydrogen linkages tend to produce tertiary and quaternary amines very quickly under typical reaction conditions, the use of such secondary amines in polyurethane and polyurea production processes has not been a commercially viable option.

In fact, some disclosures in the prior art suggest that a hydrocarbon such as polyvinyl chloride can not be used in amine displacement reactions of the type necessary to produce secondary amines. See, e.g., U.S. Pat. No. 3,933,717 at column 1, lines 31–46 where it is taught that the reactivity of such hydrocarbons is so small that it is difficult to introduce amino groups to any significant extent.

U.S. Pat. No. 4,643,953 discloses a process for the production of an electro-conductive material which is made of a dehydrohalogenated halo-organic polymer that has been reacted with a substoichiometric amount of an amine. The material produced by this process is not, however, a hydrocarbon in which the halide present in the starting polymer has been displaced by an amino group. In fact, this patent disclosure stresses that the polyvinyl chloride retains its physical properties even after reaction with the amine.

U.S. Pat. No. 5,041,668 discloses secondary aromatic diamine compounds which are prepared by the condensation of an aromatic amine with paraformaldehyde to form the corresponding imine. This imine is then reduced with $LiAlH_4$ to produce the corresponding secondary amine.

SUMMARY OF THE INVENTION

It is an object of the present invention to provide a process for the production of a secondary amine having a hydrocarbon backbone (i.e., a backbone made up of only hydrogen and carbon) in high yield.

It is also an object of the present invention to provide a process for the production of a secondary amine having a hydrocarbon backbone in high yield which process may be carried out in standard production equipment using commercially available materials.

It is a further object of the present invention to provide secondary amines having a hydrocarbon backbone, a functionality of at least 1 and a molecular weight (number average) of at least about 74.

These and other objects which will be apparent to those skilled in the art are accomplished by reacting a hydrocarbon having a good leaving group with a primary amine, a primary diamine (i.e., a compound having two primary amino groups) or ammonia at a temperature of from about 70° to about 250° C. in amounts such that at least 0.5 moles of amine are present for each equivalent of leaving group.

DETAILED DESCRIPTION OF THE PRESENT INVENTION

The present invention relates to a process for the production of secondary amines having a hydrocarbon backbone by reacting a hydrocarbon having a good leaving group with an aliphatic, cycloaliphatic or aromatic amine in amounts such that at least 0.5 moles of amine are present for each equivalent of leaving group at a temperature of from about 70° to about 250° C. The amine may be either a primary mono-amine or a primary diamine. This reaction may optionally be carried out in the presence of an acid scavenger. This invention is also directed to the secondary amines having a hydrocarbon backbone which are produced by this process and to the use of such secondary amines in the production of polyurethanes and polyureas.

As used herein, a "good leaving group" is any group which can be displaced at the carbon atom by nucleophiles such as nitrogen, oxygen, sulfur, etc. or the anions of these nucleophiles under the reaction conditions of the process of the present invention. Halides such as chloride, bromide and iodide and mesylates are particularly preferred leaving groups.

The amine hydrocarbons of this invention have a functionality of at least 1, preferably from about 2 to about 4 and a molecular weight (number average) of at least about 74, preferably from about 300 to about 4,000. They are further characterized in that substantially all of the amine groups are secondary amine groups with few, if any, tertiary amine groups.

The secondary amines having a hydrocarbon backbone of the present invention may be prepared by reacting a hydrocarbon (i.e., a compound which is made up exclusively of hydrogen and carbon with the exception of its leaving group and in which no oxygen, nitrogen, etc. linkages are present in the backbone) containing a leaving group with a primary amine or ammonia, at a temperature of from about 70° to about 250° C., optionally in the presence of an acid scavenger, such as a tertiary amine or an inorganic base such as sodium hydroxide.

The hydrocarbon with a good leaving group may be obtained by converting a hydrocarbon having a reactive group such as a hydroxyl group or an olefinic group to a suitable leaving group. This reaction may optionally be carried out in the presence of a solvent. Examples of good leaving groups include: halides, sulfonates, nitrophenoxy groups, mesylates and tosylates. Preferred leaving groups are the halides, mesylates, and tosylates. Mesylates are the most preferred leaving groups.

Hydrocarbons having reactive groups are known to those skilled in the art. Examples of suitable hydrocarbons having reactive groups include: methanol, octanol, 1,2-ethanediol, 1,4-butanediol, cyclohexane dimethanol, benzene dimethanol, polybutadienediol, pentaerythritol, sorbitol, and polyallyl alcohol.

In one method for preparing a hydrocarbon containing a halide (e.g., chloride) leaving group, a hydrocarbon containing at least one hydroxyl group may be reacted with a halogenation reagent. Suitable halogenation reagents for hydrocarbons having at least one hydroxyl group include: carbonyl chloride, thionyl chloride, triphenyl-phosphine in carbon tetrachloride, and methane sulfonyl chloride in N,N-dimethylformamide.

A hydrocarbon with a good leaving group may also be prepared by reacting a hydrocarbon containing an olefinic group with a halogenation reagent, optionally in the presence of a catalyst such as silica gel or aluminum oxide. Halogenation reagents useful in this reaction include dihalogens such as $Br_2$, $Cl_2$, ICl, etc.; thionyl halides; phosphorous halides, and hydrogen halides.

Hydrocarbons containing sulfonate as the leaving group may be prepared by reacting a hydrocarbon alcohol with methane sulfonyl chloride in the presence of a tertian/amine or amide. This reaction may be carried out at any suitable temperature but temperatures of from about −30° to about 40° C. have been found to be particularly useful. Solvents may also be used in this process. Suitable tertiay amine catalysts include: pyridine, triethylamine, tributylamine, and diazabicycio-[2,2,2]octane. Suitable amide catalysts include N,N-dimethyl formamide and N,N-dibutylformamide.

Examples of solvents useful in the production of hydrocarbons having good leaving groups include: methylene chloride, toluene, chlorobenzene, tetrahydrofuran, hexanes, dimethyl formamide and dimethyl sulfoxide.

Primary amines are reacted with the hydrocarbon containing a leaving group over a temperature range of from about 70° to about 250° C. to produce the secondary amines of the present invention. The primary amines useful in this reaction include: ammonia, aliphatic mono-amines having from 1 to 18 (preferably from 6 to 10) carbon atoms, aliphatic diamines having from 1 to 18 (preferably from 2 to 8) carbon atoms, cycloaliphatic primary mono-amines having from 4 to 12 (preferably from 6 to 8) carbon atoms, cycloaliphatic primary diamines having from 6 to 12 (preferably from 6 to 8 ) carbon atoms, aromatic primary mono-amines having from 1 to 18 (preferably from 6 to 12) carbon atoms and aromatic primary diamines having from 1 to 18 (preferably from 6 to 12) carbon atoms. These amines can be used alone or in combination. Examples of specific amines which have been found to be useful in the practice of the present invention include: butylamine, aniline, cyclohexylamine, 2-ethyl hexyl amine, 1-(2-aminoethyl) piperazine, 1,4-bis-(3-aminopropyl)piperazine, phenylene diamine, and 4,4'-methylene dianiline and mixtures thereof.

The ratio of moles of amine to equivalents of leaving group is generally from about 12:1 to about 0.5:1, preferably about 3:1.

Tertiary amines or inorganic bases may be used as acid scavengers in the reaction mixture during the amine displacement reaction of the present invention. Examples of suitable acid scavengers include: sodium bicarbonate, sodium hydroxide, potassium hydroxide, and sodium carbonate.

It is believed that the hydrocarbon leaving group undergoes a displacement reaction to give a secondary amine. If desired, any good solvent such as methylene chloride, toluene, chlorobenzene, or tetrahydrofuran (THF) can be used in any of the foregoing reactions.

The secondary amines of the present invention are obtained in high yields (i.e., yields greater than 70%). These amines are characterized by a functionality greater than 1, molecular weights of at least about 74 and the presence of substantially all amine groups as secondary amine groups, with little, if any, tertiary amine groups present.

Having thus described our invention, the following Examples are given as being illustrative thereof.

EXAMPLES

Example 1

8.32 equivalents of 1,4-cyclohexane dimethanol, 9.32 mol of triethylamine, and 1700 ml $CH_2Cl_2$ were added to a 12 liter 3-necked flask fitted with a stirrer and reflux condenser (under nitrogen). 9.32 mol of methane sulfonyl chloride were added dropwise, keeping the solution temperature at 25° C. with an ice water bath. The reaction solution was stirred at room temperature for 0.5 hours. 1 liter of 1N HCl was added to the solution with stirring. The product was filtered, washed with toluene, and dried with a nitrogen purge to obtain the mesylate as a fluffy white solid.

Example 2

0.36 equivalents of polybutadiene diol, 0.40 equivalents of triethylamine, and 200 ml of $CH_2Cl_2$ were added to a 2 liter three-necked flask equipped with a stirrer and reflux condenser (under nitrogen). 0.40 equivalents of methane sulfonyl chloride (mesyl chloride) were added dropwise, keeping the solution temperature at 25° C. with an ice bath. The solution was stirred for 0.5 hours after the mesyl chloride addition and then neutralized with sodium hydroxide. Triethylamine, solvent and water were vacuum stripped and the product was filtered. The mesylate product was a clear liquid. The composition of the product was confirmed by GC and mass spectrophotometry.

Example 3

0.123 equivalents of the 1,4-cyclohexane dimethane mesylate prepared in Example 1 were added to a 1 liter 3-necked flask fitted with a stirrer and reflux condenser. 0.369 mol of 2-ethylhexyl amine were added to the flask and the contents of the flask were heated at 150° C. for 2 hours. The solution was cooled and neutralized with 0.123 mol of sodium hydroxide. Excess amine and water were vacuum stripped and the remaining mixture was filtered. A clear, light yellow liquid having an amine number (determined by titration with 0.1N perchloric acid in glacial acetic acid) of 292 and a viscosity of 35 mPa·s was recovered. The conversion was 95% based on the amine number. The composition of the product in which substantially all amine groups were secondary amine groups was confirmed by GC and mass spectrophotometry.

Example 4

Example 3 was repeated using 0.369 mol of cyclohexylamine instead of the 2-ethylhexyl amine. The product secondary amine was a solid which had an amine number of 338.0. The degree of conversion was 92%. The composition of the product was confirmed by GC and mass spectrophotometry.

Example 5

Example 3 was repeated using the same materials in the same related amounts in a stainless steel pressure vessel using 0.369 mol of tert-butylamine instead of the 2-ethylhexylamine. The product secondary amine was a solid which had an amine number of 367. The degree of conversion was 83%. The composition of the product was confirmed by GC and mass spectrophotometry.

Example 6

The procedure of Example 3 was repeated using the same materials in the same relative amounts with the exception that 0.123 equivalents of the polybutadiene mesylate produced in Example 2 were used instead of the mesylate produced in Example 1. The product secondary amine had an amine number of 23.6 and a viscosity at 25° C. of 6350 mPa·s. The composition of the product was confirmed by the amine number.

Example 7

300 g of solid PVC (polyvinyl chloride) and 1872 g of 2-ethylhexylamine were added to a 5 liter three-necked flask equipped with a reflux condenser and stirrer (under nitrogen). The contents of the flask were heated to 135° C. The PVC dissolved in solution. This solution was then heated at 170° C. for 1 hour, cooled, and neutralized with 384 g of 50% NaOH solution. Water and excess amine were vacuum stripped and the product was filtered to yield a dark liquid with a viscosity of 13,000 mPa·s and an amine number of 250.3. The composition of the product amine (a liquid) was confirmed by means of the amine number.

Although the invention has been described in detail in the foregoing for the purpose of illustration, it is to be understood that such detail is solely for that purpose and that variations can be made therein by those skilled in the art without departing from the spirit and scope of the invention, except as it may be limited by the claims.

What is claimed is:

1. A process for preparing a secondary amine comprising reacting a hydrocarbon containing a leaving group selected from the group consisting of sulfonates and nitrophenoxy groups with a primary monoamine, primary diamine, primary polyamine or ammonia at a temperature of from about 70° to about 250° C.

2. The process of claim 1 in which the leaving group is a sulfonate or nitrophenoxy group.

3. The process of claim 1 in which the primary amine is selected from the group consisting of aliphatic amines, cycloaliphatic amines, aromatic amines and mixtures thereof.

4. The process of claim 1 wherein the primary amine is selected from the group consisting of 2-ethylhexylamine, cyclohexylamine, butylamine, 1-(2-aminoethyl)piperazine, 1,4-bis-(3-aminopropyl)piperazine and aniline.

5. The process of claim 1 in which the leaving group on the hydrocarbon is a mesylate.

* * * * *